US005536241A

United States Patent [19]

Zapol

[11] Patent Number: 5,536,241

[45] Date of Patent: Jul. 16, 1996

[54] METHODS AND DEVICES FOR RELAXING SMOOTH MUSCLE CONTRACTIONS

[75] Inventor: Warren M. Zapol, Concord, Mass.

[73] Assignee: The General Hospital Corporation, Boston, Mass.

[21] Appl. No.: 36,522

[22] Filed: Mar. 24, 1993

Related U.S. Application Data

[63] Continuation-in-part of Ser. No. 904,117, Jun. 25, 1992, abandoned, which is a continuation-in-part of Ser. No. 850,383, Mar. 11, 1992, Pat. No. 5,396,882, and Ser. No. 767,234, Sep. 27, 1991, abandoned, which is a continuation-in-part of Ser. No. 622,865, Dec. 5, 1990, abandoned.

[51] Int. Cl.$^6$ ................................................. A61M 37/00
[52] U.S. Cl. ........................... 604/23; 604/26; 604/48
[58] Field of Search .......................... 604/48, 49, 51–53, 604/891.1, 892.1, 23–26, 904; 128/200.14, 200.23, 203.12, 203.15

[56] References Cited

U.S. PATENT DOCUMENTS

| | | |
|---|---|---|
| 3,785,377 | 1/1974 | Jorgensen . |
| 4,010,897 | 3/1977 | Treharne et al. ........................ 239/8 |
| 4,287,040 | 9/1981 | Alamaro . |
| 4,297,123 | 10/1981 | Wyse et al. . |
| 4,336,798 | 6/1982 | Beran . |
| 4,534,343 | 8/1985 | Nowacki et al. . |
| 4,592,348 | 6/1986 | Waters et al. . |
| 4,667,668 | 5/1987 | Wetterlin . |
| 4,852,561 | 8/1989 | Sperry . |
| 4,877,589 | 10/1989 | O'Hara . |
| 4,915,915 | 4/1990 | Treharne et al. . |
| 4,954,526 | 9/1990 | Keefer .................................. 514/611 |
| 5,098,376 | 3/1992 | Berry et al. .............................. 604/26 |
| 5,155,137 | 10/1992 | Keefer et al. ............................ 514/611 |
| 5,208,233 | 5/1993 | Keefer et al. .......................... 514/231.8 |
| 5,396,882 | 3/1995 | Zapol ................................... 128/200.14 |
| 5,427,797 | 6/1995 | Frostell et al. ........................... 424/434 |

FOREIGN PATENT DOCUMENTS

| | | |
|---|---|---|
| 2144997 | 3/1985 | United Kingdom . |
| 2178958 | 2/1987 | United Kingdom ................. 604/48 |
| WO92/17445 | 10/1992 | WIPO . |
| WO93/12068 | 6/1993 | WIPO . |

OTHER PUBLICATIONS

Blomqvist et al., Inhaled Nitric Oxide (NO): A Selective Pulmonary Vasodilator Reversing Human Hypoxic Pulmonary Vasoconstriction (HPV), Circulation 84:361, 1991.

Desai et al., Involvement of Nitric Oxide in the Reflex Relaxation of the Stomach to Accommodate food or Fluid, Nature 351:477, 1991.

Donahoe et al., Production of $O_3$, NO, and $N_2O$ in a Pulsed Discharge at 1 Atm, Ind. Eng. Chem. 16:208–215, 1977.

Fractacci et al. Inhaled Nitric Oxide, Anesthesiology 75:990–999, 1991.

Pepke-Zaba et al., Inhaled Nitric Oxide as a Cause of Selective Pulmonary Vasodilation in Pulmonary Hypertension, The Lancet 338:1173–1174, 1991.

Rimar et al., Prolonged Duration of Inhaled Nitric Oxide Induced Vasodilation in Perfused Rabbit Lungs Circulation 84:362, 1991.

Roberts, Jr. et al., Inhaled Nitric Oxide (NO): A Selective Pulmonary Vasodilator for the Treatment of Persistent Pulmonary Hypertension of the Newborn (PPHN), Circulation 84:1279, 1991.

Dupuy et al., Bronchodilator Action of Inhaled Nitric Oxide in Guinea Pigs, J. clin. Invest. 90:421–428, 1992.

(List continued on next page.)

Primary Examiner—Randall L. Green
Assistant Examiner—V. Alexander
Attorney, Agent, or Firm—Fish & Richardson

[57] ABSTRACT

Methods and devices for using nitric oxide (NO) to decrease or prevent the contraction of a smooth muscle in a non-respiratory-tract organ of an animal, the organ being one which contains or is surrounded by a biological fluid which is not blood, which method includes the step of introducing an effective amount of NO into the fluid.

20 Claims, 4 Drawing Sheets

OTHER PUBLICATIONS

Kacmarek et al., Nitric Oxide as a Bronchodilator in Methacholilne Induced Bronchospasm in Mild Asthmatics, 1993 ALA/ATS International Conference, May 16–19, 1993, San Francisco, CA #21556 (Abstract).

Messent et al., The Pulmonary Physician and Critical Care, Thorax 47:651–656, 1992.

Swami et al., the Pulmonary Physician and Critical Care, Thorax 47:555–562, 1992.

Frostell, Md,PhD et al., Inhaled Nitric Oxide: A Selective Pulmonary Vasodilator Reversing Hypoxic Pulmonary Vasoconstriction, Circulation 83:2038–2047, 1991.

Dalby et al., Comparison of Output Particle Size Distribution from Pressurized Aerosols Formulated as Solutions or Suspensions, Pharmac. Re. 5:36–39, 1988.

Buga et al., Endothelium–Derived Nitric Oxide Relaxes Nonvascular Smooth Muscle, European J. of Pharmc. 161:61–72, 1989.

Ishii et al., A Simple and Sensitive Bioassay Method for Detection of EDRF with RFL–6 Rat Lung Fibroblasts, Am. J. Physiol. 261:H598–H603, 1991.

Stuart–Smith et al., Epithelium, contractile Tone, and Responses to Relaxing Agonists in Canine Bronchi, J. Appl. Physiol. 69:678–685, 1990.

Suzuki et al., The Relationship Between Tissue Levels of Cyclic GMP and Tracheal Smooth Muscle Relaxation in the Guinea–Pig, Clinical & Pharmacol. & Physol. 13:39–46, 1986.

Tan et al., Cigarette Smoke Activates Guanylate Cyclase and Increases Guanosine 3', 5'–Monophosphate in Tissues, Science 198:934–936, 1977.

Maron et al., Cigarette Smoke Causes Acute Fluctuations in the Cyclic GMP Content of the Isolated Intact Lung, Respiration 43:39–44, 1984.

Heaslip et al., Co–Regulation of Tracheal Tone By Cyclic AMP— and Cyclic GMP–Dependent Mechanisms, J. Pharmacl. & Experms. 243:1018–1026, 1987.

Moncada et al., Nitric Oxide: Physiology, Pathophysiology, and Pharmacology, Pharmacl. Reviews 91:109–141, 1991.

Kalant et al., Drugs and Respiratory System, Chapter 39 362–397, 1989.

Gilman et al., Vascular Effects of Cigarette Smoke in Isolated Pig Lungs, Am. Rev. Respir. Dis. 124:549–553, 1981.

Flenley, Today's Treatment of Airway Obstruction . . . and Tomorrow's?, Respiration 55:4–9, 1989.

Physicians'Desk Reference, pp. 969–971, 2322–2323, 668–670.

Edwards et al., Activation of Hepatic Guanylate Cyclase by Nitrosyl–Heme Complexes, Biomed. Pharmlgy. 30:2531–2538, 1981.

Garg et al., Nitric Oxide Generating Vasodilators Inhibit Mitogenesis and Proliferation of BALB/C 3T3 Fibroblasts by a Cyclic GMP–Independent Mechanism, Biochem. Biophysl. Re. Comm. 171:474–479, 1990.

Schmidt et al., Stimulation of Soluble Coronary Arterial Guanylate Cyclase by Sin–1, European J. Pharmaclgy. 122:75–79, 1986.

McNamara et al., Adenosine 3', 5' Monophosphate Formation by Preparation of Rat Liver Soluble Guanylate Cyclase . . . and Other Nitroso Compounds, Can. J. Physiol. Pharmacol. 58:1446–1456, 1980.

Ignarro, Biosynthesis and Metabolism of Endothelium–Derived Nitric Oxide, Annu. Rev. Pharmacol. Toxicol. 30:535–560, 1990.

Allen and Hanbury, Product Information Bulletin on Ventolin, 1990.

Boje et al., Endothelial Nitric Oxide Generating Enzyme(s) in the Bovine Aorta: Subcellular Location Location and Metabolic Characterization, Am. Soc. Pharmclgy. & Experm. Therapeutics 253:20–26, 1990.

Southern et al., Inhibition of Insulin Secretion by Interleukin–1$\beta$ and Tumor Necrosis Factor–$\alpha$ via an L–Arginine–Dependent Nitric Oxide Generating Mechanism, FEBS 276:42–44, 1990.

Garg et al., Nitric Oxide–Generating Vasodilators and 8–Bromo–Cyclic Guanosine Monophosphate Inhibit . . . Vascular Smooth Muscle Cells, J. Clin. Invest. 83:1774–1777, 1989.

Garg et al., Nitric Oxide–Generating Vasodilators Inhibit Mitogenesis and Proliferation of BALB/C 3T3 by a Cyclic GMP–Independent Mechanism, Biochem, Biophyl. Re. Comm. 171:474–479, 1990.

Brune et al., Activation of a Cytosolic ADP–Ribosyltransferase by Nitric Oxide–Generating Agents, J. Biol. Chem. 264:8455–8458, 1989.

Curran et al., Nitric Oxide and Nitric Oxide–Generating Compounds Inhibit Hepatocyte Protein Synthesis, FASEB J. 5:2085–2092, 1991.

Ignarro, Endothelium–Derived Nitric Oxide: Actions and Properties, FASEB J. 3:31–36, 1989.

Peckham, Physiologic Factors Affecting Pulmonary Artery Pressure in Infants with Persistent Pulmonary Hypertension, J. Ped. 6:1005–1010, 1978.

Zapol et al., Pulmonary Circulation During Adult Respiratory Distress Syndrome, Mercel Dekker, 241–273, 1985.

Fox et al., Pulmonary Hypertension in the Perinatal Aspiration Syndromes, Pediatrics 59:205–211, 1977.

Dworetz et al., Survival of Infants with Persistent Pulmonary Hypertension without Extracorporeal Membrane Oxygenation, Pediatrics 84:1–6, 1989.

Fishman, Pulmonary Hypertension and Cor Pulmonale, Chapter 64 pp. 999–1048.

Radermacher et al., Comparison of Ketanserin and Sodium Nitroprusside in Patients with Severe ARDS, Anesthesiology 68:152–157, 1988.

Vlahakes et al., The Pathophysiology of Failure in Acute Right Ventricular Hypertension: Hemodynamic and Biochemical Correlations, Circulation 63:87–95, 1981.

Ignarro et al., Endothelium–Derived Relaxing Factor Produced and Released from Artery and Vein is Nitric Oxide, Proc. Natl. Acad. Sci. USA 84:9265–9269, 1987.

Palmer et al., Nitric Oxide Release Accounts for the Biological Activity of Endothelium–Derived Relaxing Factor, Nature 327:524–526, 1987.

Ignarro, Biological Actions and Properties of Endothelium–Derived Nitric Oxide Formed and Released From Artery and Vein, Dept. Pharmlgy. pp. 23–278.

Higgenbottam et al., Am. Rev. Resp. Dis. Suppl. 137:107, 1988.

Zapol et al., Pulmonary Hypertension in Severe Acute Respiratory Failure, N.E. J. Med. 296:476–480, 1977.

Meyer et al., Nitric Oxide (NO), A New Test Gas for Study of Alveolar–Capillary Diffusion, Eur. Respir. J. 2:494–496, 1989.

Hounam et al., particle Deposition pp. 125–156.

Archer et al., Comparison of the Hemodynamic Effects of Nitric Oxide and Endothelium–Dependent Vasodilators in Intact Lungs, J. Appl. Physiol. 68:735–747, 1990.

Furchgott et al., Endothelium–Derived Relaxing and Contracting Factors, FASEB J. 3:2007–2018, 1989.

Archer et al., Hypoxic Pulmonary Vasoconstriction is Enhanced by Inhibition of the Synthesis of an Endothelium Derived Relaxing Factor, Biochem. Biophysl. Re. Comm. 164:1198–1205, 1989.

Brashers et al., Augmentation of Hypoxic Pulmonary Vasoconstriction in the Isolated Perfused Rat Lung by in Vitro Antagonists of Endothelium–Dependent Relaxation, J. Clin. Invest. 82:1495–1502, 1988.

Ignarro et al., Mechanism of Vascular Smooth Muscle Relaxation by Organic Nitrates, Nitrites, Nitroprusside and Nitric Oxide: . . . S–Nitrosothiols as Active Intermediates, J. Pharmol. Experm. Ther. 218:739–749, 1981.

Kadowitz et al., Pulmonary Vasodilator Responses to Nitroprusside and Nitroglycerin in the Dog, Clin. Invest. 67:893–902, 1981.

Naeije et al., Effects of vasodilators on Hypoxic Pulmonary Vasoconstriction in Normal Man, Chest 82:404–410, 1982.

Flavahan et al., Respiratory Epithelium Inhibits Bronchial Smooth Muscle Tone, J. Appl. Physiol. 58:834–838, 1985.

Hugod, Effect of Exposure to 43 ppm Nitric Oxide and 3.6 ppm Nitrogen Dioxide on Rabbit Lung, Int. Arch Occup. Environ, Health 42:159–167, 1979.

Nakajima et al., Biological Effects of Nitrogen Dioxide and Nitric Oxide, Nitrogen Oxides 121–141.

Packer, Is It Ethical to Administer Vasodilator Drugs to Patients with Primary Pulmonary Hypertension, Chest 95:1173–1175, 1989.

Agabwal et al., Nature pp. 915–916, 1965.

Stavert et al., Nitric Oxide and Nitrogen Dioxide . . . Concentrations for Brief Periods, Inhalation Toxicology 2:53–67, 1990.

Morel et al., Acute Pulmonary Vasoconstriction and Thromboxane Release During Protamine Reversal of Heparin Anticoagulation in Awake Sheep, Circulation Research 62:905–915, 1988.

Morel et al., C5α and Thromboxane Generation Associated with Pulmonary Vaso–and Broncho Constriction during Protamine Reversal of Heparin, Anesthesiology 66:597–604, 1987.

Borland et al., A Simultaneous single Breath Measurement of Pulmonary Diffusing Capacity with Nitric Oxide and Carbon Monoxide, Eur. Respir. J. 2:56–63, 1989.

Altabef et al., Intravenous Nitroglycerin for Uterine Relaxation of an Inverted Uterus, Am. J. Obstet. Gynecol. 166:1237–1238, 1992.

Oxytocin. Protaglandins. Ergot Alkaloids. Tocolytic Agents., Chapter 39, pp. 942–945.

Resnick et al., Evaluation and Medical Management of Urinary Incontinence, Anesthesia pp. 3–6, 1992.

Zapol et al., Regional Blood Flow During Simulated Diving in the Conscious Weddel Seal, J. Appl. Physiol. 47:968–973, 1979.

PCT Search Report from the corresponding PCT Patent Application No. PCT/US93/06091.

METHODS AND DEVICES FOR RELAXING SMOOTH MUSCLE CONTRACTIONS

The invention was made in the course of work supported by the U.S. Government under NIH grant no. HL42397; the U.S. Government therefore has certain rights in the invention.

This application is a continuation-in-part of Zapol, U.S. Ser. No. 07/904,117, filed Jun. 25, 1992, now abandoned, which in turn is a continuation-in-part of Zapol, U.S. Ser. No. 07/850,383, filed Mar. 11, 1992, U.S. Pat. No. 5,396,882, and of Zapol et al., U.S. Ser. No. 07/767,234, filed Sep. 27, 1991, now abandoned, which in turn is a continuation-in-part of Zapol et al., U.S. Ser. No. 07/622,865 filed Dec. 5, 1990 (now abandoned), all of which applications are herein incorporated by reference.

BACKGROUND OF THE INVENTION

The field of the invention is treatment to reduce or prevent smooth muscle contraction, especially with respect to the musculature of an organ such as a uterus or a urinary bladder.

In certain situations, notably premature labor, the uterine musculature is triggered by various stimuli to contract at a time when it is undesirable or even life-threatening to do so. If the fetus is near term but has not yet produced the surfactant that will enable it to breathe properly after birth, quieting uterine contractions and thereby delaying delivery for a few days may be sufficient: during those few days, the mother is treated with cortisol to induce immediate surfactant production by the fetus, which can then be delivered without the threat of developing the often-fatal condition known as hyaline membrane disease. In other cases, labor may begin so early in gestation that it must be controlled for weeks or even months to permit the fetus to mature in utero adequately to survive outside the womb. Present methods of preventing uterine contractions in cases of premature labor or other circumstances in which delay of delivery is desirable include mechanical suturing of the cervix (circlage) in early pregnancy, bed rest, and/or intravenous treatment with a tocolytic agent such as a $\beta_2$ adrenergic agonist (e.g., ritodrine, terbutaline, metaproterenol, albuterol or fenoterol); magnesium sulfate; ethanol; a calcium channel antagonist (e.g., nifedipine); or an inhibitor of prostaglandin synthesis (e.g., indomethacin). [Goodman and Gilman's The Pharmacological Basis of Therapeutics (7th Ed.) Gilman et al., ed.; Macmillan Publishing Co., N.Y., 1985, pages 942–943.] In addition, the use of intravenous nitroglycerin (an NO donor compound) has been reported to relax a postpartum uterus (Altabef et al., Am. J. Obstet. Gynecol. 166:1237–1238, 1992). Such drugs, however, have certain systemic side effects that may be unpleasant or harmful to the mother, and possibly to the fetus.

In an analogous manner, the often painful constrictions of urinary bladder musculature associated with the presence of an indwelling urinary catheter are typically relieved with intravenous smooth muscle relaxants that frequently cause undesired systemic effects (Resnick and Yalla, Chapter 14 in *Campbell's Urology*, 6th Ed., W. B. Saunders Co., 1992, pages 652–655).

SUMMARY OF THE INVENTION

The invention features methods and devices for using nitric oxide (NO) to decrease or prevent the contraction of smooth muscle in vivo. The methods involve introducing an effective amount of NO into a biological fluid which contacts the target smooth muscle, or which contacts a membrane or other biological structure adjacent to the target muscle and through which the NO can readily diffuse to reach the muscle. Because hemoglobin rapidly combines with NO, rendering it unavailable to relax smooth muscle, the biological fluid cannot be blood and preferably contains no more than trace amounts of red cells. An "effective amount" of NO is an amount which, when mixed in the volume of biological fluid which applies in a given case, gives a concentration of NO in the immediate vicinity of the target smooth muscle sufficient to cause relaxation of the muscle: i.e., a concentration preferably at least approximately 0.01 µM; more preferably between 0.1 and 1000 µM; and most preferably between 1 and 100 µM (e.g., approximately 10 µM). Where the volume of biological fluid into which the NO is diluted is small (e.g., the mucus within a non-pregnant uterus, or the fluid within an eye), a smaller absolute amount of NO will be required than where the volume of fluid is large (e.g., the amniotic fluid of a near-term pregnancy). In addition, where mixing of the NO with the biological fluid is relatively inefficient (e.g., where the fluid is relatively viscous), the rate of diffusion of NO through the fluid may be poor from the point at which the NO is introduced into the fluid to the point at which it exerts its biological effect on the musculature of the target organ, requiring a larger absolute amount of NO to achieve therapeutic concentrations in the vicinity of the muscle, or careful introduction of the NO near the location of the muscle. The concentration of NO in the source of NO, which determines the maximum equilibrium concentration of NO that can be achieved in the biological fluid, can vary widely. Gaseous NO can be provided, for example, as pure NO [$10^6$ parts per million (ppm)], which would give a theoretical maximum equilibrium concentration (tmec) in aqueous solution at 37° C. and at atmospheric pressure of approximately 1–2 mM. However, because NO is potentially toxic in high concentrations, pure NO may be deemed too dangerous to work with on a routine basis. Alternatively, the NO gas may be diluted in a carrier gas to between 1 to 100,000 ppm (preferably 10 to 10,000 ppm, and more preferably 100–1000 ppm), which would decrease proportionately the tmec achievable in the biological fluid (e.g., the tmec for a biological fluid exposed to 100 ppm NO at 37° C. and atmospheric pressure is 0.1–0.2 µM). Where the source of NO is a liquid into which NO has been dissolved, rather than a gas, the amount of NO in the liquid will be limited by the solubility of NO in the liquid used. Certain types of non-aqueous carrier liquids, such as those known to be capable of dissolving large quantities of oxygen ($O_2$), could carry an amount of NO some 30 times as high as the amount achievable in aqueous solutions; examples include fluorocarbon liquid such as FX-80, organic oils, organic solvents such as ethanol and glycerol, organic polymer liquids, and silicone.

One embodiment of the method of the invention is intended for decreasing or preventing the contraction of a smooth muscle in a hollow organ (preferably a non-respiratory tract organ) of an animal (e.g., a mammal such as a human), which organ contains a biological fluid which is not blood; this method involves introducing an effective amount of NO directly or indirectly into that biological fluid. By "non-respiratory tract organ" is meant an organ which does not form any part of the respiratory tract of the animal. Examples of relevant types of smooth muscle contractions in such hollow organs include uterine contractions, muscle spasms in the wall of a urinary bladder or small intestine, contractions of sphincter muscles, and vascular smooth muscle spasms of a retinal blood vessel of an eye. Where the target organ is a uterus, the uterine contraction may be associated with, for example, premature labor or uterine cramps, and the target biological fluid may be the amniotic fluid of a pregnant uterus or the mucus secretions present inside a non-pregnant uterus. Although NO would not be able to penetrate the blood-rich placenta and so cannot act on that portion of the uterus (approximately 10% of the full term uterus) which is covered by placenta, it is believed that the other structures of the uterine wall between the amniotic fluid and the uterine musculature (the amnion, chorion and decidua vera) will not present a significant barrier to the diffusion of NO from the amniotic fluid to the muscle cells. The total thickness of these structures ranges from about 1 cm at the fourth month of pregnancy to 1 or 2 mm at term (Cunningham et al., *Williams' Obstetrics,* 18th Edition, 1989: Appleton-Lange, Norwalk, Conn.; pages 53 and 56); NO is a small, lipid-soluble molecule that diffuses readily through cellular membranes and the interstices between cells.

The method may also be used to counter the constriction of a blood vessel the exterior surface of which is bathed by or otherwise in contact with a non-blood fluid: for example, blood vessels in the brain or spinal cord which are accessible to NO that has been introduced into the cerebrospinal fluid. This method is particularly useful for reversing vascular smooth muscle spasms associated with transient ischemic attacks (TIA), reperfusion injury, infarction, stroke, or migraine headaches. Likewise, NO introduced into amniotic fluid would dilate both placental (fetal) and uterine (maternal) blood vessels by relaxing the vascular smooth muscle contacted by the amniotic fluid, thus enhancing both fetal gas transport and maternal perfusion to the uterus.

The NO may be dissolved in a pharmaceutically acceptable carrier liquid prior to introduction into the biological fluid of the target organ, and then injected directly into the organ to mix with the biological fluid present therein. Carrier liquids that would be useful for this purpose include standard saline solutions, aliquots of the biological fluid extracted from the organ and mixed ex vivo with NO, and liquids such as fluorocarbons or organic solvents [in which NO exhibits a high level of solubility (Shaw and Vosper J. Chem. Soc. Faraday Trans. 1. 73:1239–1244, 1977; Young, Solubility Data Series 8:336–351, 1981), so that a large concentration of NO can be delivered in a small volume of carrier]. The liquid may alternatively contain a polymerizable compound such as silicone (dimethylsiloxane) or a plastic (e.g. acrylate resin); when such an NO- and polymerizable compound-containing liquid is mixed, just prior to injection, with a reagent which catalyzes the polymerization of the compound, it remains liquid during the injection process, but then forms within the target organ a spagetti-like solid that is too bulky, for example, to be ingested by a fetus. NO slowly diffuses out of the solid, which acts like a reservoir of NO constantly replenishing the supply of NO within the organ.

Alternatively, a pharmaceutically acceptable solid material [such as small plastic pellets or an intrauterine device (IUD)] may be impregnated with NO (e.g., by exposure to NO gas), and then injected or otherwise implanted into the target organ. As above, the solid material acts as a reservoir or source of NO to maintain a desired concentration of NO in the biological fluid inside the target organ.

Another means for introducing NO into the target organ is by injecting it in its gaseous state: either as pure NO gas, or NO in a mixture of gases including one or more pharmaceutically acceptable carrier gases. The carrier gas is preferably carbon dioxide ($CO_2$), which will readily dissolve in the biological fluid with no harmful physiological effects, but may instead be another relatively inert gas such as nitrogen ($N_2$). The carrier gas preferably is not pure oxygen ($O_2$), which rapidly combines with NO to form toxic nitrogen dioxide ($NO_2$).

Rather than injecting or implanting the source of NO directly into the target organ, one can utilize the ability of NO to diffuse across a gas-permeable material. Examples of such materials include gas-permeable membranes such as those used in blood oxygenators (e.g., dimethylpolysiloxane or polyalkylsulfone), and microporous materials such as Gore-tex™ or Celgard™, which allow gas molecules such as NO to pass through its micropores to dissolve in liquid. In preferred embodiments, a section of this material is configured with one face in contact with the biological fluid and a second face in contact with a source of NO, separating the fluid from the source of NO but permitting individual molecules of NO gas to pass through and diffuse into the fluid. This can be accomplished in various ways. For example, an inflatable "balloon" (such as the balloon on a Foley catheter) made of a gas-permeable material can be inserted into the organ and inflated with an NO-containing gas or liquid. Alternatively, a hollow tube or fiber (e.g., a "capillary") constructed of a gas-permeable material can be inserted into the target organ so that the exterior surface of the capillary is in contact with the biological fluid within the organ, while the lumen of the capillary is filled with or in communication with a source of NO. Possible sources of NO include a pressurized mixture of gases including NO; a liquid (such as a fluorocarbon) in which gaseous NO is dissolved; and an aqueous solution of an NO-donor compound that can spontaneously decompose in aqueous solution to release NO into the solution, including but not limited to S-nitroso-N-acetylpenicillamine, S-nitrosocysteine, nitroprusside, nitrosoguanidine, and $Na(O_2N_2\text{—}NEt_2)$. When an aqueous solution of such a compound is used as the source of NO, the gas-permeable material is preferably one which is permeable to NO but not to the NO-donor compound itself, since it is desirable to prevent the risks (e.g., systemic vasodilation, decreased blood pressure, and lung edema) potentially associated with systemic distribution of such NO-donor compounds.

The NO-containing gas or liquid is passed through the capillary, permitting NO to diffuse directly into the biological fluid in situ. By adjusting the concentration of NO in the source gas or liquid, the concentration of NO in the target biological fluid and the resulting biological effect on the target organ can be tightly controlled. If desired, the flow of NO-containing perfusing gas or liquid can be halted, or the NO temporarily removed from the perfusing gas or liquid, allowing the NO present in the target organ to dissipate gradually with the device still in place and ready to resume immediate treatment as needed.

Alternatively, the procedure can be carried out ex vivo, with a portion of the biological fluid (1) periodically (tidally) or continuously withdrawn from the target organ, (2) contacted with a section of gas-permeable material (e.g., a capillary or cluster of capillaries) through which NO passes from a source of NO, and (3) returned to the organ via a needle or catheter. The invention thus also includes a device for carrying out these procedures, which device includes (a) a source of NO; and (b) a section of gas-permeable material having a first and a second face, the first face being configured to be placed in contact with the biological fluid and the second face being in communication with the source of NO, the section of material separating the fluid from the source of NO but permitting NO to diffuse through the material from the second face to the first face. If the section of gas-permeable material is in the form of a capillary or cluster of capillaries, the device may be configured to have the fluid contact the outside of the capillary and the source of NO within the capillary, or vice versa. The section of gas-permeable material may be configured to be implanted directly in the target organ, with the first face in contact with the fluid within the organ; or it may be configured to be utilized ex vivo, with the first face in communication with the lumen of a tube through which the biological fluid can be drawn out of the target organ and into contact with the first face; the latter device would include a mechanism such as a syringe or pump for accomplishing this drawing action, and would preferably also include a mechanism for returning the biological fluid to the organ either via the same tube through which it was withdrawn from the organ, or through a second tube, after the fluid has contacted the gas-permeable material. The source of NO may be a liquid or a gas; if a gas, the device preferably includes a mechanism such as a valve for controllably releasing the NO-containing gas mixture to contact the gas-permeable material.

The invention also includes an implantable device such as an IUD which contains an NO-releasing compound such as S-nitroso-N-acetylpenicillamine, S-nitrosocysteine, nitroprusside, nitrosoguanidine, $Na(O_2N_2-NEt_2)$, nitroglycerine, isoamyl nitrite, inorganic nitrite, azide, or hydroxylamine, which compound is held within a chamber (e.g., the lumen of a tube) having a wall made of a solute-permeable material (for example, cellulose acetate) that permits the NO-releasing compound to dialyze or diffuse slowly out of the chamber into the fluid of the organ in which the device is implanted. The NO-releasing compound may be stored in the chamber in its dry (i.e., powdered or crystalline) state, or may be in aqueous solution. Upon decomposition of the NO-releasing compound (either spontaneously or as the result of contact with endogenous enzymes or other biological molecules present in the fluid of the organ), NO released by the NO-releasing compound acts on the smooth muscle in the organ just as in the embodiments described above. The target organ for this particular embodiment of the invention is preferably an organ having a relatively small total volume of non-blood biological fluid: e.g., a non-gravid uterus, urinary bladder, ureter, or a portion of the gastrointestinal tract. Although this embodiment of the invention results in the presence of an NO-releasing compound in the biological fluid, with the potential for uptake of the compound into the circulatory system, systemic effects resulting from such uptake, if any, will be minimal. This is because the total volume of biological fluid of the target organ is relatively small (i.e., less than a liter, and preferably less than 0.5 liter), so a high concentration of the NO-releasing compound can be achieved in the target organ with a relatively small amount of the NO-releasing compound. The larger the volume of fluid in the organ, the greater the amount of NO-releasing compound that must be used to achieve a therapeutic concentration, and the greater the potential for uptake of significant amounts into the bloodstream. This device will also be useful for reversing or preventing vasoconstriction in an organ containing a non-blood biological fluid, again provided that the total volume of such fluid in the target organ is relatively small, to keep the effects local.

The methods and devices of the invention offer a number of advantages over standard means of controlling smooth muscle contraction. In the standard treatment, the intravenous drugs used (e.g., $\beta_2$ agonists and, very recently, nitroglycerine) act systemically, introducing undesirable side effects such as diffuse vasodilation with a concomitant drop in blood pressure to possibly dangerous levels, rapid heart beat, and lung edema. While NO can act as a potent smooth muscle relaxant, as has been shown in numerous in vitro studies and in the in vivo studies on lungs disclosed in Zapol et al., U.S. Ser. No. 07/622,865 now abandoned, and Ser. No. 07/767,234, now abandoned, its biological effects are solely local ones, because any NO which enters the bloodstream is immediately inactivated by reaction with hemoglobin. Furthermore, the method of the invention induces an immediate relaxation of the target muscle as soon as it is contacted with NO, a response which can be readily and minutely calibrated by adjusting the amount of NO delivered into the target organ at any given time; this response can be maintained as long as the NO supply is maintained, and discontinued soon after treatment is withdrawn, without long-term effects. The biological effects of NO can therefore be precisely controlled both temporally and with respect to their intensity and their site of action within the patient.

Other features and advantages of the invention will be apparent from the following description of the preferred embodiments, and from the claims.

DESCRIPTION OF THE PREFERRED EMBODIMENTS

EXAMPLE 1

Figure 1:
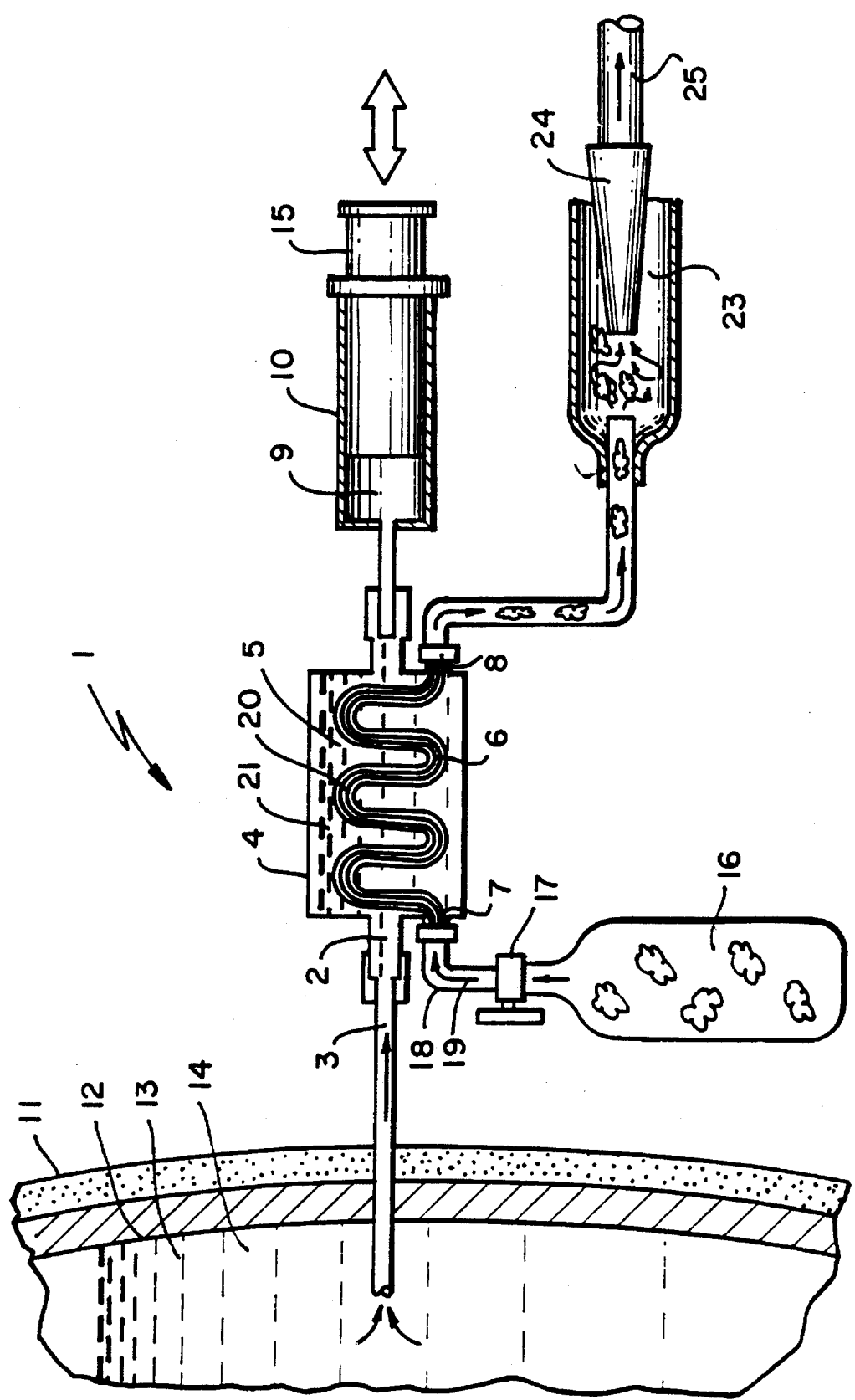
FIG. 1 illustrates a diagrammatic cross-sectional view of an extracorporeal gas dialyzer unit that is one embodiment of the device of the invention.

Shown in FIG. 1 is an extracorporeal gas dialyzer unit 1 with a tube 2 connecting a needle 3 and a housing 4, which housing defines a chamber 5 containing a bundle of interwoven microporous capillaries 6 having an inlet port 7 and an outlet port 8. Chamber 5 is in communication with the lumen of barrel 9 of a syringe pump 10. Needle 3 is placed with local infiltration anesthesia across the abdominal wall 11 or via the cervix into the amniotic sac 12 within the uterine cavity 13 of a pregnant patient, to provide access to the amniotic fluid 14. Outward movement of the plunger 15 within barrel 9 of syringe pump 10 creates a partial vacuum within barrel 9, which causes amniotic fluid to be withdrawn via needle 3 and tube 2 into chamber 5. A source of NO gas 16 is connected via reducing valve 17 and tube 18 to inlet port 7. Opening valve 17 permits a stream of NO 19 to travel through tube 18, entering the capillaries 6 at inlet port 7 and exiting at outlet port 8 as waste gas (which can be scavenged, for example, by being emptied into an open reservoir chamber 23 that is aspirated by a nozzle 24 attached to a vacuum line 25). During its passage through the capillaries 6, some of the NO diffuses through the gas-permeable material of the capillary walls 20, and into the amniotic fluid 21 in contact with the capillaries 6. The direction of movement of plunger 15 is then reversed, thereby applying pressure that forces the NO-rich amniotic fluid 21 out of chamber 5, returning it to the uterine cavity 13 through tube 2 and needle 3. This procedure is repeated as many times as are necessary to achieve the desired concentration of NO in the amniotic fluid within the uterine cavity, and may be continuously performed for as long as the patient's condition dictates. Typically, unit 1 will be sized to withdraw approximately 10–20 ml of amniotic fluid 13 with each repetition, and each repetition will take approximately 5 sec to perform. Movement of the plunger 15 may be accomplished manually or by motorized means; where many repetitions are envisioned, generally only the latter will be practicable. The concentration of NO in the gas stream 19 may be varied as desired, with a higher concentration (e.g., $10^4$–$10^6$ ppm) producing a higher concentration of NO in the biological fluid, resulting in a more rapid and profound relaxation of the uterine musculature than will a lower gaseous NO concentration (e.g., $10^0$–$10^3$ ppm). The gas-permeable material may be a microporous material made of a polymer such as tetrafluoroethylene (Teflon™) or polypropylene, manufactured in a way that generates submicroscopic pores (e.g., approximately 20 Å) in the polymer. Such microporous materials are available commercially (e.g., Gore-tex™, available from Gore Assoc., Inc., and Celgard™, available from Celanese Corp.). Alternatively, the gas-permeable material may be a membrane formed from a synthetic polymer such as thin (e.g., 5 micron) silicone rubber, which permits gases such as NO to diffuse through it not by means of static pores, but rather by thermal rearrangement within the polymer itself. Diffusion through such membranes takes place as follows: A molecule of NO dissolves in the membrane at the side of the membrane in contact with the gas phase; it then diffuses through the membrane to the other side (the side in contact with amniotic fluid) through a process that depends on the formation of "channels" in the polymer network due to thermal agitation of the chain segments; and finally the NO is desorbed into the fluid. These and other materials which allow the diffusion of NO into the fluid phase of the device may be formed into hollow fibres for use as the capillaries 6; such hollow fibres are widely used in such applications as extracorporeal membrane oxygenators, which maintain blood oxygen and carbon dioxide levels during open heart surgery. Typically the capillaries are interwoven to increase turbulence and mixing in the fluid flowing over them, thereby increasing the efficiency of gas transport into the fluid.

The syringe pump 10 and housing 4 can be constructed of any standard material suitable for such applications, such as glass, plastic, or noncorrosive metal, or a combination thereof, and the needle 3 would preferably be of a size suitable for aspirating amniotic fluid, e.g., 16 or 18 guage, optionally fitted with a catheter. Although causing the gas phase to flow through the interior of the capillaries 6 and the amniotic fluid to flow around them is the preferred arrangement, the device may alternatively be designed to direct the fluid through the capillaries 6 and the gas into the space around the capillaries 6. Particulate matter in the amniotic fluid can be prevented from entering the chamber 5 by placing a filter (50–200 micron pore size) in tube 2.

EXAMPLE 2

Figure 2:
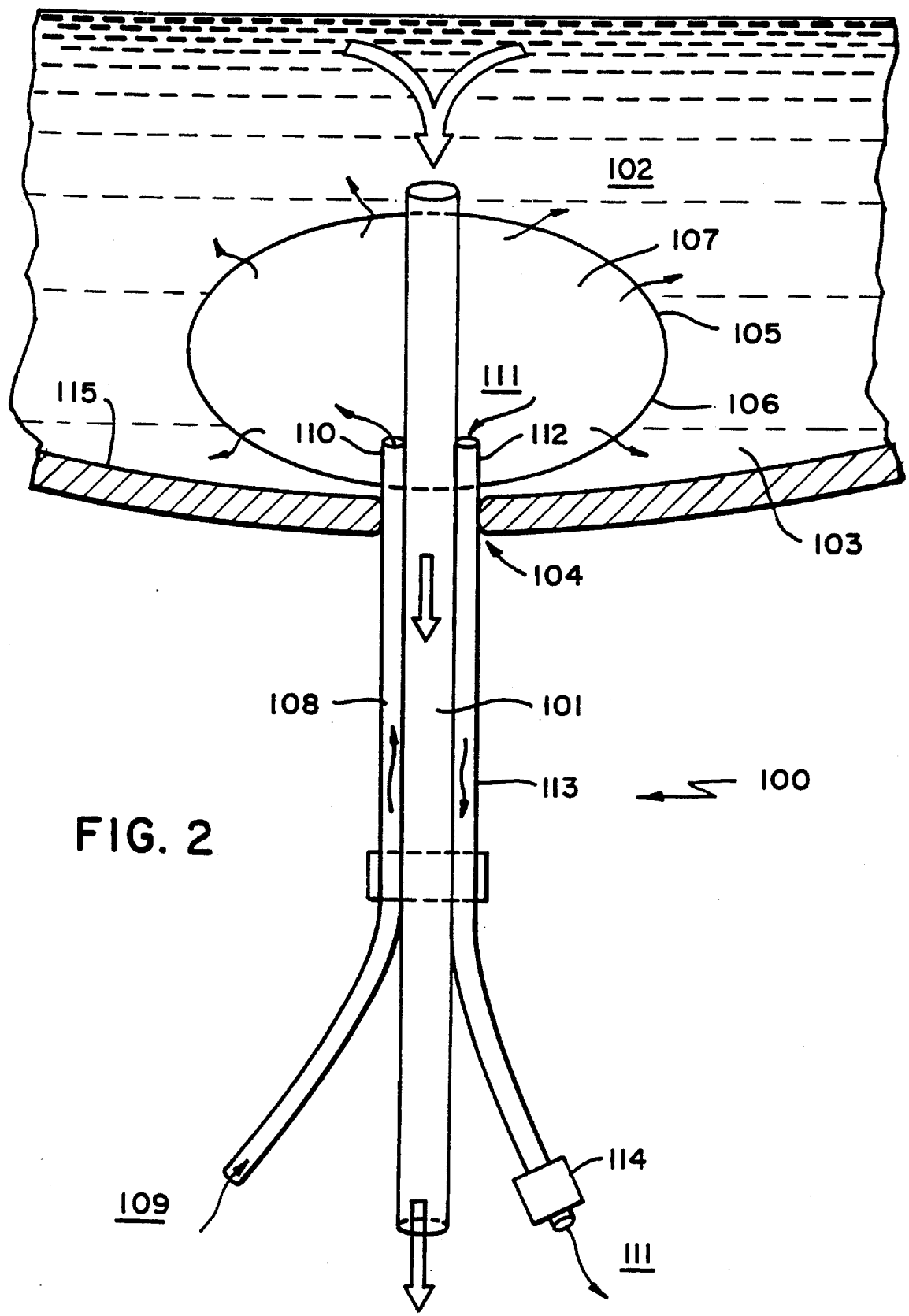
FIG. 2 illustrates a diagrammatic cross-sectional view of a device for delivering NO to a urinary bladder.

Illustrated in FIG. 2 is an indwelling Foley catheter adapted to deliver NO into a urinary bladder, for treatment or prevention of inappropriate constriction of the bladder musculature (detrusor hyperactivity) or the ureters: for example, the painful bladder muscle (detrusor) spasms sometimes experienced by paraplegic patients or ureteral spasms after ureteral surgery. As shown in FIG. 2, the catheter unit 100 has a tube 101 for withdrawal of urine 102 from the bladder cavity 103 through the urethral orifice 104. The tube 101 is held in place in the bladder cavity 103 by means of an attached inflatable balloon 105 having a gas-permeable wall 106 defining a chamber 107. A second tube 108 in communication with a positive pressure source of NO-containing gas or liquid 109 opens into the chamber 107 of the balloon 105, permitting NO-containing gas or liquid 109 to flow through tube 108 and out opening 110 into the balloon chamber 107. Excess gas or liquid 111 exits balloon 105 by flowing into opening 112 of a third tube 113, to be discarded or recycled as appropriate. In order to maintain balloon 105 in an inflated state, the gas or liquid 111 exits from tube 113 under positive pressure (e.g. 30 cm $H_2O$) via a positive pressure check valve 114. Some NO present in the gas or liquid 109 in chamber 107 passes through the gas-permeable wall 106 into the urine 102 that is in contact with wall 106, and then diffuses through the urine 102 to the bladder or ureter wall 115. When removal of unit 100 from bladder cavity 103 is desired, balloon 105 is deflated by stopping the flow of gas or liquid through tube 108 and disconnecting the positive pressure check valve 114, then extracting, through tube 113, any residual gas or liquid 109 present in chamber 107. The device 100 can be placed in a patient's bladder via the urethra, or directly in the bladder via a cystotomy.

EXAMPLE 3

Figure 3A:
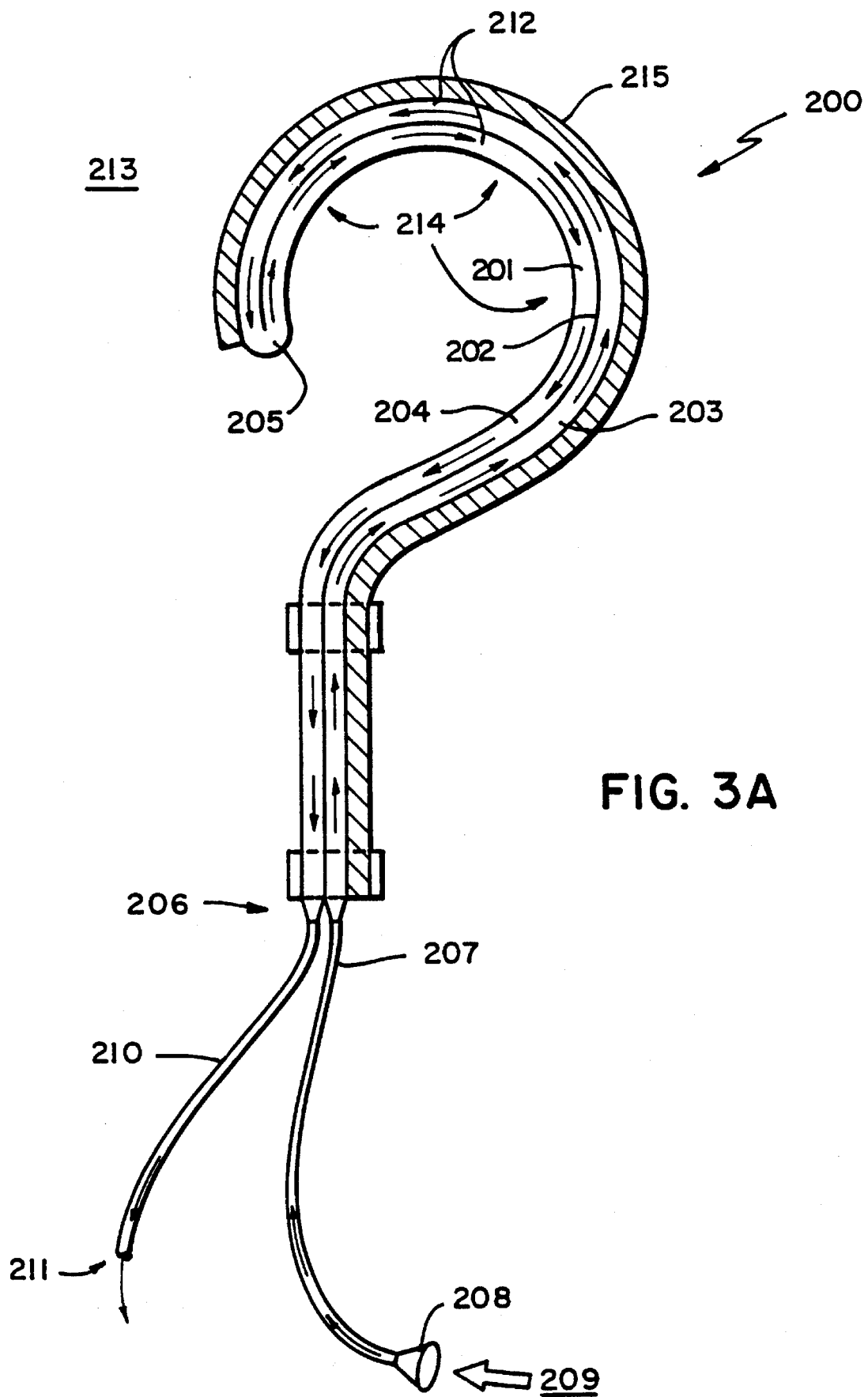
FIGS. 3A and 3B illustrate two diagrammatical cross-sectional views of an intrauterine device (IUD) for delivering NO to a non-pregnant uterus.
Figure 3B:
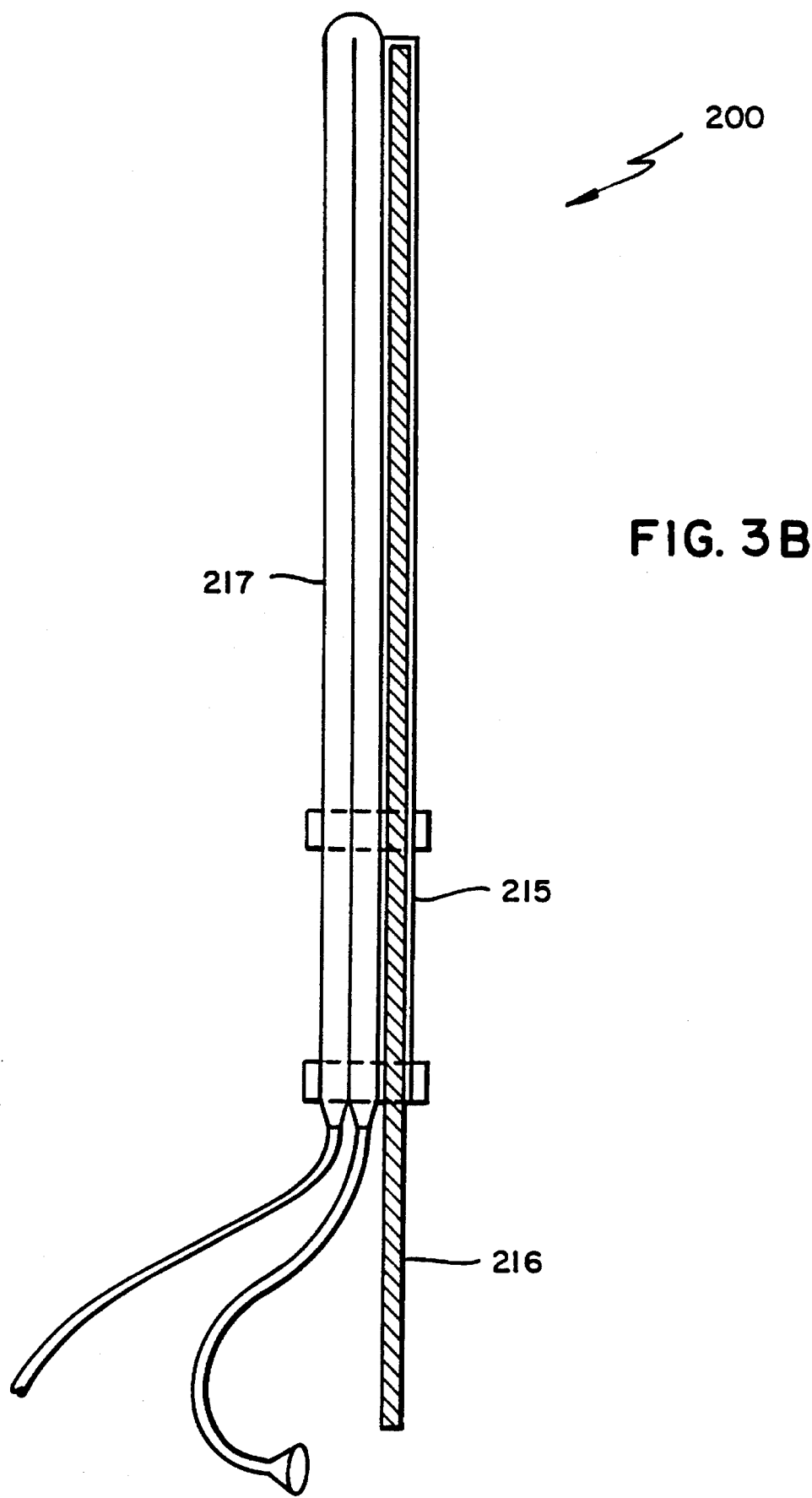

FIGS. 3A and 3B illustrate one embodiment of the intrauterine device (IUD) of the invention: FIG. 3A is a cross section of the device 200 as it appears following insertion into a non-gravid uterus, while FIG. 3B indicates the conformation of the same device prior to insertion into a uterus.

As shown in FIG. 3A, device 200 includes a double lumen tube 201 enclosing a septum 202 defining two continuous channels, an inlet channel 203 and an outlet channel 204, which channels communicate at end 205. Tube 201 is closed at end 205. At end 206, inlet channel 203 is in communication with an inlet tube 207 having an injection tip 208 shaped to permit ready injection of a liquid into the lumen of inlet tube 207. When an NO-containing liquid or gas 209 is injected (e.g., by syringe) into injection tip 208, the liquid 209 flows through inlet tube 207 and into inlet channel 203. At end 205 the liquid 209 enters outlet channel 204, flowing through outlet channel 204 and then through outlet tube 210, which is in communication with outlet channel 204. The liquid 209 then exits outlet tube 210 at opening 211, and can be discarded or collected as desired. The walls of tube 201 have a gas-permeable face 212 through which NO can pass. When the NO-containing liquid 209 passes through the inlet channel 203 and outlet channel 204, NO present in the liquid 209 passes through the gas-permeable face 212 and into the surrounding uterine environment 213. A curved shape 214 is imposed on device 200 by a sleeve 215 running the length of tube 201, which sleeve is made of a flexible plastic having a "memory" for the curved shape 214.

FIG. 3B shows the same device 200 prior to insertion into a uterus. A rigid rod 216 inserted into the lumen of sleeve 215 forces the device 200 into a straight, extended conformation 217 suitable for insertion through a cervix and into a uterine cavity. Withdrawing rod 216 from sleeve 215 permits sleeve 215 to revert to the curved shape 214 as shown in FIG. 3A, which shape helps prevent device 200 from being expelled from the uterus.

Other Embodiments

Other embodiments are within the claims below. For example, the source of NO can be an aqueous solution of an NO-donor compound (such as S-nitroso-N-acetylpenicillamine, S-nitrosocysteine, nitroprusside, nitrosoguanidine, Na(O$_2$N$_2$—NEt$_2$), nitroglycerine, isoamyl nitrite, inorganic nitrite, azide, or hydroxylamine) which is sealed inside the device prior to implantation into the target organ. Furthermore, the target organ can vary widely. Organs appropriate for treatment with the methods and devices of the invention are ones in which the target smooth muscles are bathed with a non-blood biological fluid, such as urine, mucus, cerebrospinal fluid, or digestive juices, which fluid preferably contains no more than trace amounts of red blood cells. The usefulness of the method of the invention for relaxing the smooth muscle in the wall of a given hollow organ can be easily tested by the following means:

The internal hydrostatic pressure in the organ is measured by standard means (e.g., strain guage and catheter) well known to those skilled in the art. Baseline contractions would be induced by pharmacologial means (e.g., i.v. pitocin to contract a uterus; i.v. methacholine to contract a bladder; or i.v. cholicystokinin to contract a gallbladder). The organ would then be treated with escalating doses of NO by adding an NO-containing liquid or gas directly to the interior fluid, or by inserting a balloon into the lumen of the organ, and inflating the balloon with an NO-containing liquid or gas. At each dosage level, contractions would be induced as described above. The peak pressure of the contractions should be markedly reduced in the presence of NO compared to in the absence of NO, since the musculature of the target organ will be relaxed by NO treatment.

If relaxation and vasodilation of the vascular smooth muscle of a target organ is the desired response, then blood flow to the organ can be measured at baseline and then again after treatment with NO as above, at which point the blood flow should have increased. The preferred method of measuring regional organ blood flow is by serial left atrial injections of radiolabelled microspheres, as described in Zapol et al. (J. Appl. Physiol.: Respirat. Environ. Exercise Physiol. 47:968–973, 1979).

Where the target organ is within the gastrointestinal tract, treatment can be as follows:

Regions of the stomach, small intestine or colon that can be reached by a tube with radiologic or fiberoptic guidance can be perfused with an NO-containing solution. This would distend the stomach, intestine or bowel with an NO-containing solution that would both vasodilate and reduce contractions of the target muscle. A standard double lumen nasogastric tube could be employed, injecting and continuously draining NO-containing saline. Alternatively, a fill-and-clamp technique with intermittent drainage can be used. The NO-containing fluid can be localized in a given portion of the gastrointestinal tract (e.g., a portion of the bowel that is in spasm, or in the vicinity of a constricted sphincter) to permit local effects where desired. This localization can be accomplished, for example, by the use of inflatable balloons strategically located on the double lumen nasogastric tube, which balloons act to trap the NO-containing liquid in a defined region of the gastrointestinal tract, or by injecting the NO-containing liquid into the desired region via the lumen of a fiber-optic gastroscope or colonoscope. Alternatively, a long, tubular modification of the urological balloon catheter described above (and shown in FIG. 2) could be placed at a desired point in the G.I. tract (e.g., in the bowel), and then inflated with an NO-containing liquid or gas, permitting NO to diffuse through the gas-permeable wall of the balloon and into the bowel lumen. The method of the invention is useful for reversing vasoconstriction, thus augmenting blood flow and protecting against ischemic bowel injury resulting from vasoconstriction within the G.I tract. It is also useful for dilating constricted bowel regions and thereby preventing spasm, contractions, and cramping pain: for example, in regional enteritis, colitis, etc. The mucosa lining the target gastrointestinal organ, like the mucosa lining the repiratory system (Zapol et al., U.S. Ser. No. 07/767,234 now abandoned) should not present a significant barrier preventing diffusion of NO into the organ's musculature.

The method can also be adapted for treatment of vasoconstriction in the eye, as is sometimes observed following eye surgery, or in central nervous system or spinal blood vessels. NO can be directly introduced into the cerebrospinal fluid or the fluid of the eye by any appropriate means: e.g., by injection of an NO-containing liquid, or by implantation of a gas-permeable capillary that is perfused with NO-containing gas or liquid, or by tidal aspiration and equilibration with NO gas. As noted previously, treatment in accordance with the invention should have no systemic effects, since any NO taken up by the blood would be bound by hemoglobin and thus inactivated.

What is claimed is:

1. A device for relaxing smooth muscle of a hollow organ, the organ being a non-respiratory tract organ containing a non-blood biological fluid, said device comprising a source of nitric oxide (NO); and a section of gas-permeable material having a first and a second face, said first face being configured to be placed in contact with the fluid and said second face being in communication with said source of NO, said section separating the fluid from said source of NO, wherein NO can diffuse through the material from said second face to said first face.

2. The device of claim 1, wherein said NO is in gaseous form, and said device additionally comprises a mechanism for controllably releasing said NO to contact said second face.

3. The device of claim 1, wherein said section of gas-permeable material is configured to be implanted in the organ, with said first face in contact with the fluid within the organ.

4. The device of claim 3, wherein said NO is in gaseous form, and said device additionally comprises a mechanism for controllably releasing said NO to contact said second face.

5. The device of claim 3, wherein NO$_2$ is substantially absent from said source of NO.

6. The device of claim 3, wherein O$_2$ is substantially absent from said source of NO.

7. The device of claim 3, wherein said source of NO is a liquid in which gaseous NO is dissolved.

8. The device of claim 3, wherein said source of NO is an aqueous solution of an NO-releasing compound.

9. The device of claim 1, wherein said first face is in communication with the lumen of a tube through which the fluid can be drawn out of the organ and into contact with said first face, said device further comprising a mechanism for accomplishing said drawing.

10. The device of claim 9, wherein said device further comprises a mechanism for returning the fluid to the organ through said tube after the fluid has contacted said first face.

11. The device of claim 9, wherein said device further comprises a second tube through which the fluid is returned to the organ after the fluid has contacted said first face.

12. The device of claim 9, wherein said NO is in gaseous form, and said device additionally comprises a mechanism for controllably releasing said NO to contact said second face.

13. The device of claim 9, wherein NO$_2$ is substantially absent from said source of NO.

14. The device of claim 9, wherein $O_2$ is substantially absent from said source of NO.

15. The device of claim 9, wherein said source of NO is a liquid in which gaseous NO is dissolved.

16. The device of claim 9, wherein said source of NO is an aqueous solution of an NO-releasing compound.

17. The device of claim 1, wherein nitrogen dioxide ($NO_2$) is substantially absent from said source of NO.

18. The device of claim 1, wherein oxygen ($O_2$) is substantially absent from said source of NO.

19. A device for relaxing smooth muscle in an organ, the organ being a non-respiratory tract organ containing a non-blood biological fluid, said device comprising a housing defining a chamber; and an NO-releasing compound contained within said chamber, said chamber having a wall comprising solute-permeable material through which said NO-releasing compound can diffuse, said wall being configured to be placed in contact with the biological fluid.

20. The device of claim 19, wherein said NO-releasing compound is selected from the group consisting of S-nitroso-N-acetylpenicillamine, S-nitrosocysteine, nitroprusside, nitrosoguanidine, $Na(O_2N_2-NEt_2)$, nitroglycerine, isoamyl nitrite, inorganic nitrite, azide, and hydroxylamine.

* * * * *